(12) United States Patent
Hansen et al.

(10) Patent No.: US 10,149,955 B2
(45) Date of Patent: *Dec. 11, 2018

(54) LARYNGEAL MASK

(71) Applicant: AMBU A/S, Ballerup (DK)

(72) Inventors: Jan Guldberg Hansen, Greve (DK); Troels Nicolaj Qvist, Roskilde (DK); Peer Hoffmann, Stenløse (DK); Erik Øllgaard Vilhelmsen, Espergærk (DK); Lasse Kjeld Gjøske Petersen, Frederiksværk (DK)

(73) Assignee: AMBU A/S, Ballerup (DK)

( * ) Notice: Subject to any disclaimer, the term of this patent is extended or adjusted under 35 U.S.C. 154(b) by 312 days.

This patent is subject to a terminal disclaimer.

(21) Appl. No.: 14/973,859

(22) Filed: Dec. 18, 2015

(65) Prior Publication Data
US 2016/0101254 A1  Apr. 14, 2016

Related U.S. Application Data

(63) Continuation-in-part of application No. 14/699,260, filed on Apr. 29, 2015, now Pat. No. 9,889,264, (Continued)

(51) Int. Cl.
*A61M 16/04* (2006.01)
(52) U.S. Cl.
CPC .... *A61M 16/0447* (2014.02); *A61M 16/0409* (2014.02); *A61M 16/0415* (2014.02); *A61M 16/0445* (2014.02); *A61M 16/0497* (2013.01)
(58) Field of Classification Search
CPC .......... A61M 16/04–16/0459; A61M 16/0463; A61M 16/0475–16/0486
See application file for complete search history.

(56) References Cited

U.S. PATENT DOCUMENTS

| 4,509,514 A | 4/1985 | Brain |
| 4,995,338 A | 2/1991 | Morita et al. |

(Continued)

FOREIGN PATENT DOCUMENTS

| CN | 2882657 | 3/2007 |
| CN | 101057994 | 10/2007 |

(Continued)

OTHER PUBLICATIONS

International Search Report issued by the European Patent Office in related International Application No. PCT/DK2013/050201, dated Mar. 25, 2014, 3 pages.

(Continued)

*Primary Examiner* — Valerie L Woodward
(74) *Attorney, Agent, or Firm* — Faegre Baker Daniels LLP

(57) ABSTRACT

A laryngeal mask for use in a patient includes an airway tube having an inner lumen and a distal end; and a mask portion connected at a proximal end thereof to the distal end of the airway tube and having a distal tip opposite the proximal end. The mask portion includes an inflatable cuff including an anterior cuff surface configured to contact the patient's tissue when the inflatable cuff is inflated; and a wedge portion including a stabilization surface and two walls connected to the inflatable cuff and extending therefrom toward the stabilization surface, the stabilization surface extending from the distal tip of the mask portion toward the distal end of the airway tube at a wedge angle of between about 12 and 30 degrees, the wedge angle formed between the stabilization surface and the anterior cuff surface when the inflatable mask is inflated, whereby the stabilization surface is transversely and longitudinally substantially flat to stabilize the laryngeal mask in use. The laryngeal mask has a gastric tube with a varying inner tube diameter.

12 Claims, 12 Drawing Sheets

Related U.S. Application Data which is a continuation-in-part of application No. PCT/DK2013/050201, filed on Jun. 20, 2013.

(56) References Cited

U.S. PATENT DOCUMENTS

| | | |
|---|---|---|
| 5,241,956 A | 9/1993 | Brain |
| 5,391,248 A | 2/1995 | Brain |
| 5,632,271 A * | 5/1997 | Brain .................. A61M 16/04 128/207.15 |
| 2003/0037790 A1* | 2/2003 | Brain .................. A61M 16/04 128/207.14 |
| 2003/0051734 A1 | 3/2003 | Brain |
| 2004/0020491 A1 | 2/2004 | Fortuna |
| 2004/0089307 A1 | 5/2004 | Brain |
| 2005/0081861 A1 | 4/2005 | Nasir |
| 2006/0207601 A1 | 9/2006 | Nasir |
| 2008/0099026 A1 | 5/2008 | Chang |
| 2011/0023890 A1 | 2/2011 | Baska |
| 2011/0220117 A1 | 9/2011 | Dubach |
| 2011/0226256 A1* | 9/2011 | Dubach ............... A61M 16/04 128/207.14 |
| 2011/0277772 A1 | 11/2011 | Nasir |
| 2012/0211010 A1 | 8/2012 | Brain |
| 2013/0239959 A1 | 9/2013 | Brain |
| 2013/0269689 A1 | 10/2013 | Brain |
| 2015/0114400 A1* | 4/2015 | Dubach ............... A61M 16/04 128/207.15 |
| 2015/0128946 A1 | 5/2015 | Stix |
| 2015/0144134 A1 | 5/2015 | Dubach |
| 2016/0008562 A1 | 1/2016 | Sagales |

FOREIGN PATENT DOCUMENTS

| | | |
|---|---|---|
| CN | 201832255 | 5/2011 |
| WO | WO/1997/12640 | 4/1997 |
| WO | WO 2001/024860 | 4/2001 |
| WO | WO/2004/089453 | 10/2004 |
| WO | WO/2008/001724 | 3/2008 |
| WO | WO/2012/049448 | 4/2012 |
| WO | WO/2013/079902 | 6/2013 |
| WO | WO 2014/202078 | 12/2014 |
| WO | WO 2017/103071 | 6/2017 |

OTHER PUBLICATIONS

Office Action (Chinese language), issued by the Chinese Patent Office, dated Sep. 2, 2016, for related Chinese patent application No. 201380077481X, 8 pages.

English translation of Office Action, issued by the Chinese Patent Office, dated Sep. 2, 2016, for related Chinese patent application No. 201380077481X, 7 pages.

International Search Report issued by the International Searching Authority in related International Patent Application No. PCT/EP2016/081384, dated Feb. 22, 2017; 5 pages.

Written Opinion issued the International Searching Authority in related International Patent Application No. PCT/EP2016/081384, dated Jun. 22, 2017; 5 pages.

Non-Final Office Action issued by the U.S. Patent and Trademark Office, dated Sep. 26, 2018, for related U.S. Appl. No. 14/898,424; 22 pages.

* cited by examiner

LARYNGEAL MASK

CROSS-REFERENCE TO RELATED APPLICATIONS

This application is a continuation-in-part of U.S. patent application Ser. No. 14/699,260, filed on Apr. 29, 2015, issued as U.S. Pat. No. 9,889,264 on Feb. 13, 2018, which is a continuation-in-part of International Application No. PCT/DK2013/050201, filed on Jun. 20, 2013, both entitled "A Laryngeal Mask". The disclosures of said applications are incorporated herein by reference in their entirety. This application is related to U.S. patent application Ser. No. 14/898,424, filed Dec. 14, 2015, which is a 371 application of International Application No. PCT/DK2013/050201. This application is also related to U.S. Patent Application No. 62/269,179, filed Dec. 18, 2015, and International Application No. PCT/EP2016/081384, which claim priority therefrom.

TECHNICAL FIELD

The present disclosure relates to laryngeal masks. More particularly, the present disclosure relates to laryngeal masks with stabilization features and a gastric tube for endoscopic procedures.

BACKGROUND OF THE DISCLOSURE

Laryngeal masks are used in connection with the establishment of passage of air to the respiratory tracts, while simultaneously blocking the respiratory air passage to the oesophagus. The laryngeal mask is shaped such that it has a lumen within a mask portion arranged at the distal end of an airway tube, i.e. the end of the airway tube facing towards the laryngeal opening, when the laryngeal mask is correctly placed in a patient and the cuff inflated. Around that lumen a generally elliptical, inflatable, peripheral cuff is provided, so as to form a seal around the laryngeal opening when the laryngeal mask is correctly placed in a patient and the cuff inflated. In order to be able to inflate the cuff, an inflation tube is connected to an inflation means, such as a balloon and a valve outside the patient. Operating the inflation means allows the peripheral cuff of the laryngeal mask to be inflated thereby ensuring a tight abutment of the laryngeal mask. Using the valve, the peripheral cuff may be deflated when the laryngeal mask is no longer needed and has to be removed from the patient.

Optionally, the laryngeal mask may be fitted with a passage for allowing access to the oesophagus through the mask. The passage may be utilized to evacuate or drain gastric content, to insert an instrument, or for other purposes.

Laryngeal masks generally exhibit mirror symmetry. The gastric tube may extend in the central anterior/posterior plane along the back of the airway tube all the way to the back of the inflatable cuff. The gastric tube may also be bifurcated, extending along either side of the airway tube in mirror image symmetry, and joining in the central plane just before the gastric tube passes through the cuff.

Though this mirror symmetry is largely desired to match the human body, mirror symmetry presents manufacturing drawbacks. Additionally, it is desirable to cost-effectively manufacture laryngeal masks that will remain in place even as the patient's head or the patient are moved, without unduly stressing the patient.

SUMMARY OF DISCLOSED EMBODIMENTS

The present disclosure relates to laryngeal masks. In one embodiment, a laryngeal mask for use in a patient comprises an airway tube having an inner lumen and a distal end; and a mask portion connected at a proximal end thereof to the distal end of the airway tube and having a distal tip opposite the proximal end. The mask portion comprises an inflatable cuff including an anterior cuff surface configured to contact the patient's tissue when the inflatable cuff is inflated; and a wedge portion including a stabilization surface and two walls connected to the inflatable cuff and extending therefrom toward from the stabilization surface, the stabilization surface extending from the distal tip of the mask portion toward the distal end of the airway tube at a wedge angle of between about 12 and 30 degrees, the wedge angle formed between the stabilization surface and the anterior cuff surface when the inflatable mask is inflated, whereby the stabilization surface is transversely and longitudinally substantially flat to stabilize the laryngeal mask in use.

In another embodiment, the airway tube has an inner lumen, an outer surface, a proximal end, a distal end, a curved section between the proximal end and the distal end and a gastric tube which extends along the outer surface of the airway tube. The gastric tube has a first inner diameter along at least a portion of the curved section of the airway tube, which first inner diameter is larger than a second inner diameter of the gastric tube distal to the curved section of the airway tube.

In a variation thereof, the wedge angle is between about 15 and 25 degrees.

In another variation thereof, the stabilizing surface has a minimum width aspect ratio of between about 5% and 15%, the minimum width aspect ratio being the ratio, expressed as a percentage, of the minimum width w2 to the length l of the stabilizing surface.

In a further variation thereof, the stabilizing surface has a maximum width aspect ratio of between about 22% to 35%, the maximum width aspect ratio being the ratio, expressed as a percentage, of the maximum width w1 to the length l of the stabilizing surface.

In a yet further variation thereof, the laryngeal mask comprises a recess on one side of the mask portion and a gastric tube received in the recess. The inflatable cuff has an inner volume and comprises a proximal aperture. The gastric tube penetrates through the proximal aperture and the inner volume.

BRIEF DESCRIPTION OF THE DRAWINGS

The above-mentioned and other disclosed features, and the manner of attaining them, will become more apparent and will be better understood by reference to the following description of disclosed embodiments of the invention taken in conjunction with the accompanying drawings, wherein.

In the foregoing summary and the following description the left-hand side and the right-hand side will be understood as corresponding to the left-hand side and the right-hand side of the patient when the laryngeal mask is correctly inserted into the patient. Analogously, terms such as front/anterior and back/posterior are to be understood in corresponding sense, i.e. as they would commonly be used in relation to the patient. Furthermore, "proximal" refers to the end of the laryngeal mask near the intubating professional during insertion of the laryngeal mask and "distal" refers to the end of the laryngeal mask away from the intubating professional.

DETAILED DESCRIPTION OF DISCLOSED EMBODIMENTS

The embodiments described below are merely exemplary and are not intended to limit the invention to the precise forms disclosed. Instead, the embodiments were selected for description to enable one of ordinary skill in the art to practice the invention.

Figure 13:
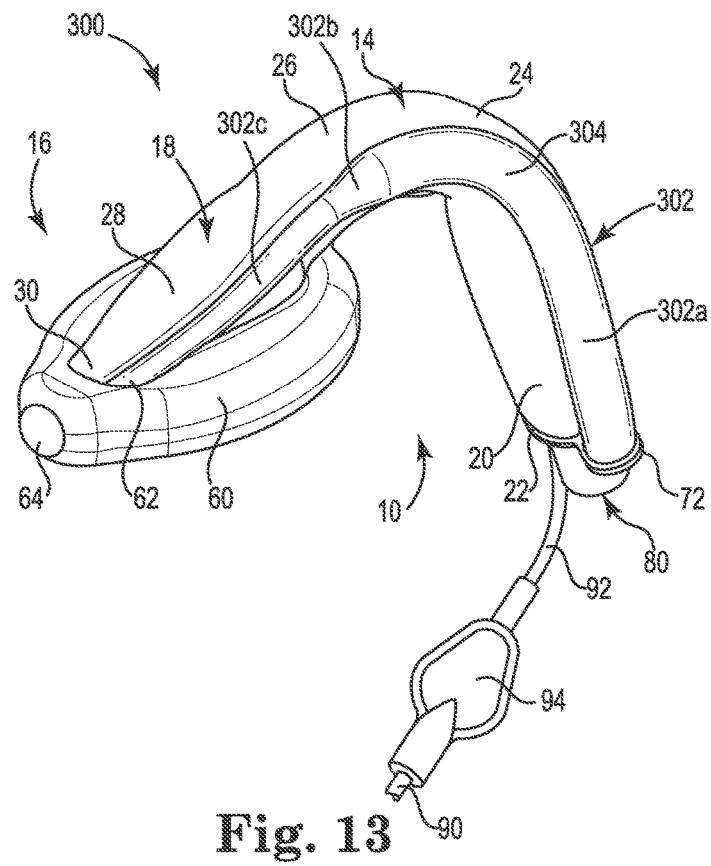
FIG. 13 is a right-side perspective view of further embodiment of a laryngeal mask including a gastric tube providing a gastric passage.
Figure 14:
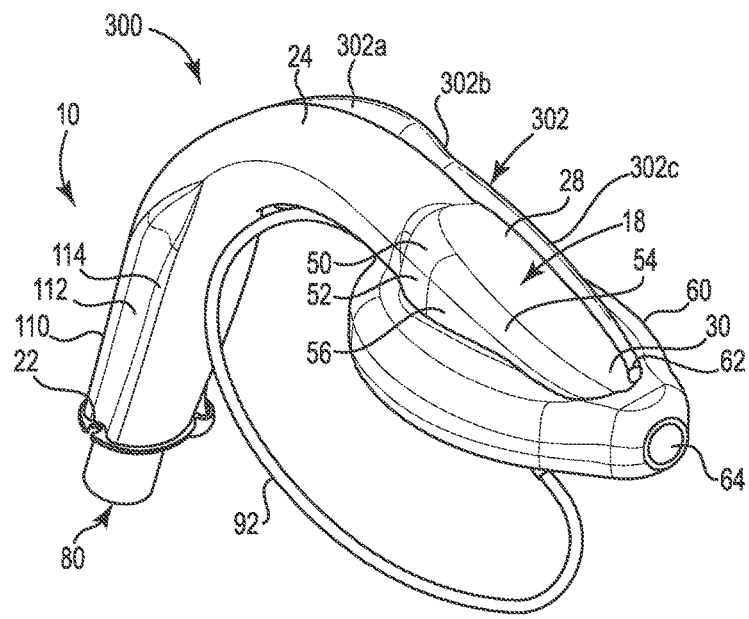
FIG. 14 is a left-side perspective view of the laryngeal mask of FIG. 13.
Figure 15:
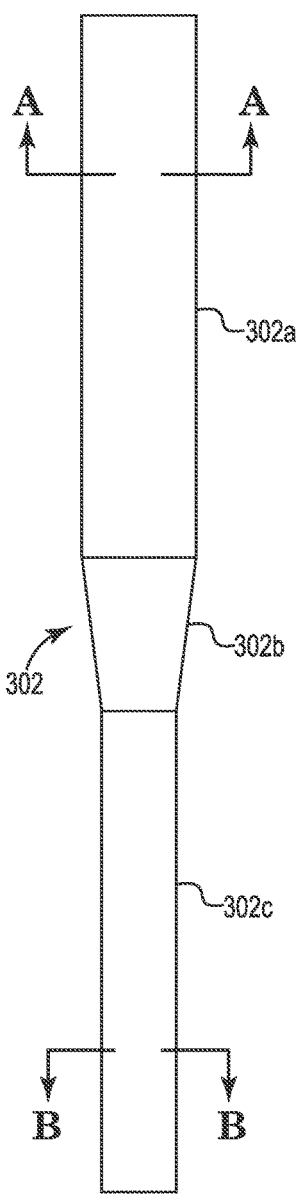
FIG. 15 is a side-view of a gastric tube according to the embodiment of FIGS. 13 and 14.
Figure 16:
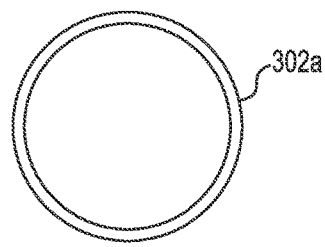
FIG. 16 is an enlarged cross-sectional view of the gastric tube along the line A-A of FIG. 15.
Figure 17:
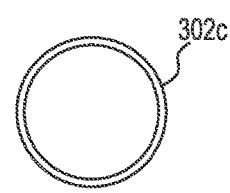
FIG. 17 is an enlarged cross-sectional view of the gastric tube along the line B-B of FIG. 15.

FIGS. 1-9 are views of an embodiment of a laryngeal mask according to the invention, denoted by numeral 10, including views of laryngeal mask 10 assembled with a gastric tube 70 providing a gastric passage and partially assembled without gastric tube 70. Laryngeal mask 10 comprises an airway tube 14 and a mask portion 16 having a substantially wedge portion 18 having a substantially stabilizing surface 28. In use, stabilizing surface 28 abuts the back of the patient's laryngopharynx as the patient or the patient's head is turned, thereby maintaining a sufficient seal of mask portion 16 on the anterior (front) side of the patient's laryngopharynx to maintain adequate ventilation of the patient. Characteristics of wedge portion 18 which make it suitable for the stabilization function are described at least with reference to FIGS. 11 and 12. These characteristics may include, in addition to a stabilizing surface, alone or in various combinations, wedge angle, maximum width aspect ratio, minimum width aspect ratio, and width ratio. FIGS. 13 and 14 are views of an embodiment of a laryngeal mask wherein a proximal section of the gastric tube has an increased inner diameter. Characteristics of the gastric tube which makes the embodiment advantageous for conducting endoscopic procedures are shown in FIGS. 15-17.

In some embodiments, the stabilization surface extends from a distal tip of the mask portion toward the distal end of the airway tube at a wedge angle of between about 12 and 30 degrees, the wedge angle formed between the stabilization surface and an anterior cuff surface when the inflatable mask is inflated, whereby the stabilization surface is transversely and longitudinally substantially flat to stabilize the laryngeal mask in use. The anterior cuff surface contacts the patient's tissue when the inflatable cuff is inflated and the laryngeal mask is in place during use. By transversely and longitudinally substantially flat it is meant that the stabilization surface may exhibit a small degree of curvature without deviating from the teachings herein. For example, the curvature radius of the stabilization surface in a transverse direction may be twice the minimum radius of the lumen of the breathing tube. Since the curvature is the reciprocal of the curvature radius, the transverse surface is flatter than the internal surface of the laryngeal tube along its posterior side. More preferably, the curvature radius is more than thrice the minimum radius of the lumen of the breathing tube. In some examples, the stabilization is longitudinally substantially flat, meaning that if a straight line is drawn from the beginning to the end of the stabilization surface along its central plane, the longest distance normal to the line between the line and the stabilization surface will be no more than ¼ the length of the stabilization surface. Thus, if the stabilization surface is 8 centimeters long, the maximum distance between the stabilization surface and the line will be about 2 centimeters. Preferably the longest distance will be no more than about ⅙ the length, and even more preferably the longest distance will be no more than about ⅛ the length.

In a variation thereof, the wedge angle is between about 15 and 25 degrees. In the case where the stabilization surface exhibits some curvature, the wedge angle may be determined by performing a least-squares fit to the stabilization surface, essentially finding a plane that dissects the stabilization surface with the least error, the angle between the plane and the anterior cuff surface forming the wedge angle.

Figure 1:
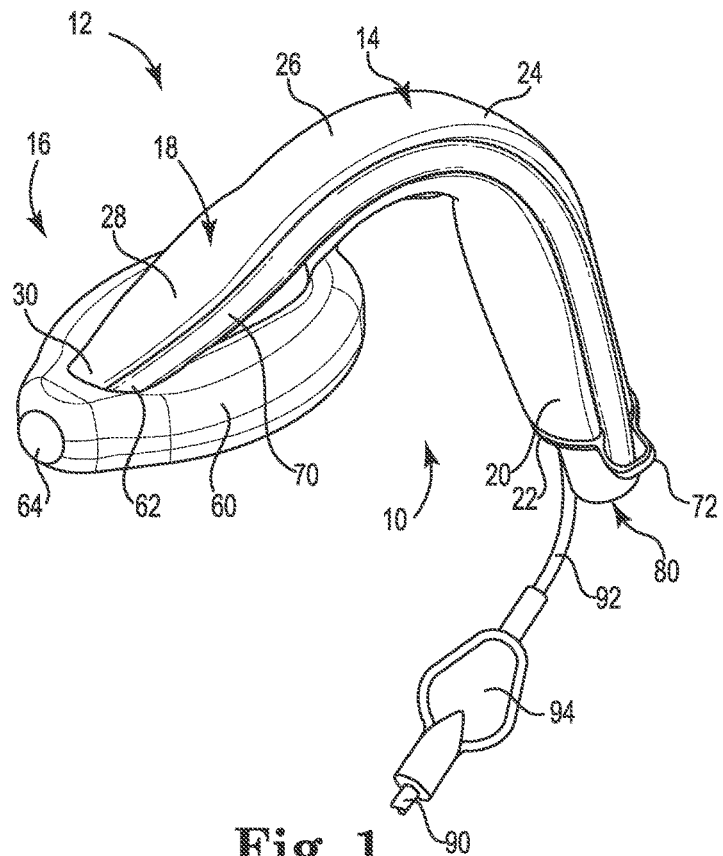
FIG. 1 is a right-side perspective view of an embodiment of a laryngeal mask including a gastric tube providing a gastric passage.
Figure 6:
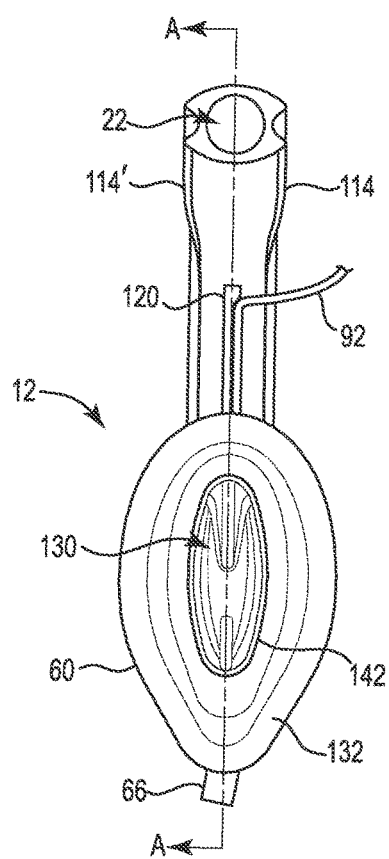
FIG. 6 is a front view of the laryngeal mask of FIGS. 1 and 2 without the gastric tube.
Figure 7:
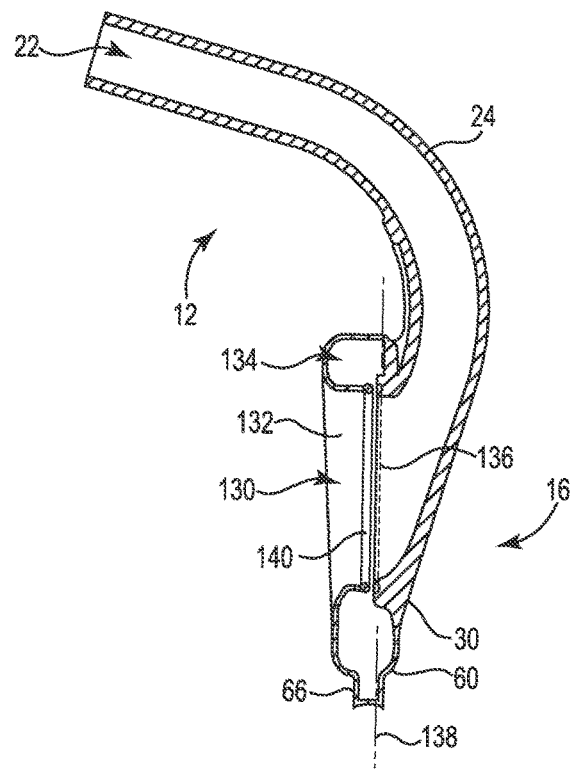
FIG. 7 is a longitudinal cross section of the laryngeal mask of FIGS. 1 and 2 taken along a plane indicated by line A-A in FIG. 6.

Turning first to FIG. 1, a perspective view of laryngeal mask 10 is shown. Airway tube 14 comprises a predetermined curvature between a proximal end 20 and a distal end 26. As best seen in FIGS. 6 and 7, airway tube 14 has an inner lumen 22 extending from proximal end 20 of airway tube 14 through a middle portion 24 to distal end 26. Distal end 26 of airway tube 14 connects to mask portion 16 having a distal end 30. Inner lumen 22 of airway tube 14 extends to a mask lumen 130 of mask portion 16, best seen in FIGS. 6 and 7, establishing fluid communication between proximal end 20 of laryngeal mask 10, which is accessible to the intubation professional as laryngeal mask 10 is inserted into the patient, and the trachea of the patient, thus providing a through-passage via which air may be supplied to and removed from the lungs of the patient during respiration. Even further, inner lumen 22 and mask lumen 130 are sized and configured to allow intubation of an endotracheal tube therethrough while laryngeal mask 10 is positioned in the patient. As shown, laryngeal mask 10 further comprises a proximal connector 80 having a distal end inserted into inner lumen 22 and a proximal end protruding therefrom and providing a contact surface for a supply tube connectable to a breathing bag adapter or a ventilation machine to complete a breathing circuit therefrom to mask lumen 130.

Mask portion 16 comprises a circumferential, inflatable cuff 60 arranged so as to surround and delimit mask lumen 130. Cuff 60 may be inflated (and deflated) via an inflation tube 92. In one example, the inflation tube extends along the outer surface of airway tube 14. Inflation tube 92 connects with cuff 60 at its distal end (not visible) and with attachment means 90 at its proximal end. Attachment means 90 allows connection with a suitable inflation means (shown in FIG. 6), such as a syringe, to inflate cuff 60 with a suitable amount of air. An inflatable pressure unit 94 is inflated when cuff 60 is inflated and enables the intubation professional to visually or tactably determine whether the pressure in cuff 60 is adequate to form a seal without unnecessarily pressing the patient's tissue. As described below with reference to FIG. 3, cuff 60 comprises a proximal aperture 62 and a distal aperture 64. Gastric tube 70 is inserted through proximal aperture 62 and distal aperture 64 and bonded to cuff 60 to seal proximal aperture 62 and distal aperture 64, thereby permitting gastric tube 70 to pass through cuff 60 without diminishing the ability to inflate cuff 60.

Airway tube 14 and mask portion 16, including cuff 60 and wedge portion 18, are preferably molded as a single piece body, denoted by numeral 12, cuff 60 being formed by gluing parts thereof together subsequent to molding. FIG. 7 shows a longitudinal cross-section of single piece body 12 as molded, i.e. before the parts of cuff 60 are glued together and before gastric tube 70 is attached.

Figure 2:
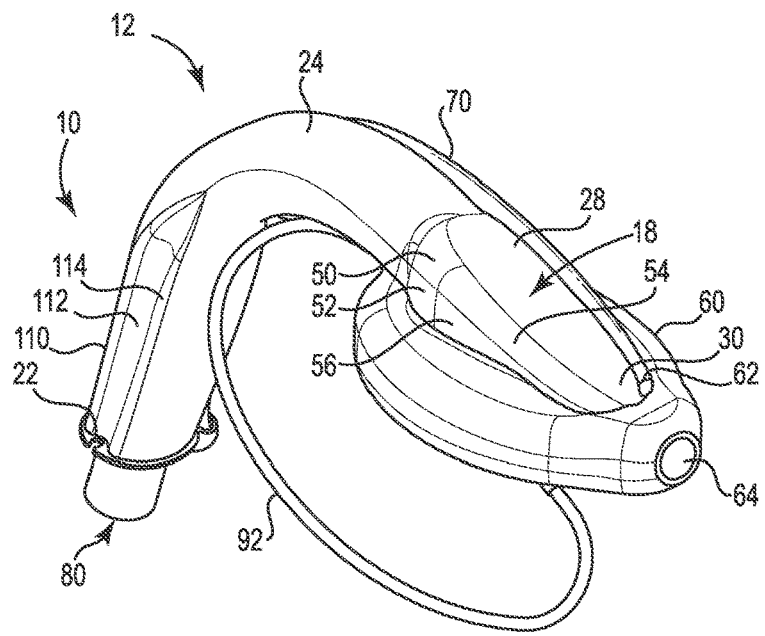
FIG. 2 is a left-side perspective view of the laryngeal mask of FIG. 1.

Referring now to FIG. 2, wedge portion 18 comprises stabilizing surface 28, a left shoulder surface formed by a left rounded shoulder wall 50 adjacent a left shoulder wall 52, and a left edge surface formed by a left rounded edge wall 54 adjacent a left edge wall 56. On the right side, there is a right shoulder wall 52' longitudinally adjacent a right edge wall 56' (best seen in FIG. 9). In the embodiment described with reference to FIGS. 10-12, a mask portion 206 is symmetrical and comprises, in addition of the left shoulder surface and the left edge surface, a right shoulder surface formed by a right rounded shoulder wall 50' adjacent right shoulder wall 52', and a right edge surface formed by a right rounded edge wall 54' adjacent right edge wall 56'. The dimensions of right shoulder wall 52' and right edge wall 56' may vary slightly between the shown embodiments to reflect the presence of gastric tube 70, which may have different diameters and thus may affect said dimensions. The dimensions of the walls described hereinabove may be characterized by wedge angle, maximum width aspect ratio, minimum width aspect ratio, and width ratio rather than specific measurements to reflect different laryngeal mask sizes suitable for differently sized patients, from pediatric to adult patients.

As used herein, "stabilizing surface" refers to a surface which does not "roll" laterally on the posterior side of the laryngopharynx in use. The stabilizing surface may be flat, both along its length and width, may be transversely flat and longitudinally curved, and may exhibit some transverse curvature as well.

Returning to FIG. 2, in the present embodiment proximal end 20 of airway tube 14 comprises longitudinal protrusions 110, 114 forming a recess 112 therebetween. On the opposite (right) side, laryngeal mask 10 comprises a longitudinal recess 100 suitable to receive gastric tube 70. Longitudinal recess 100 extends from a proximal recess portion 102 defined by longitudinal protrusions 110', 114' at proximal end 20 to a distal recess portion 104 at distal end 30. The depth of the recess may vary. The depth at middle portion 24 may be sufficient to blend or fade the external surfaces of breathing tube 14 and gastric tube 70 without presenting an edge that could irritate the patient's tissue. In one variation of the present embodiment, longitudinal recess 100 comprises recesses 102, 104 without a middle recess therebetween. In a variation of the present embodiment without a gastric tube, longitudinal protrusions 110, 110', 114, and 114', and recess 100, are not present.

Figure 3:
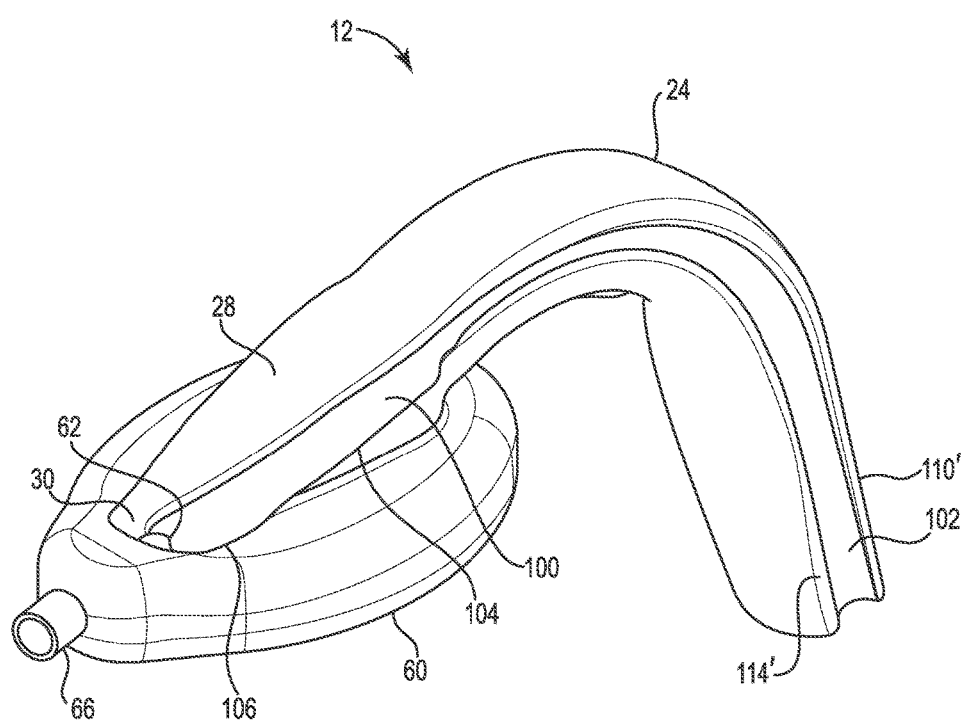
FIG. 3 is a right-side perspective view of the laryngeal mask of FIGS. 1 and 2 without the gastric tube.
Figure 4:
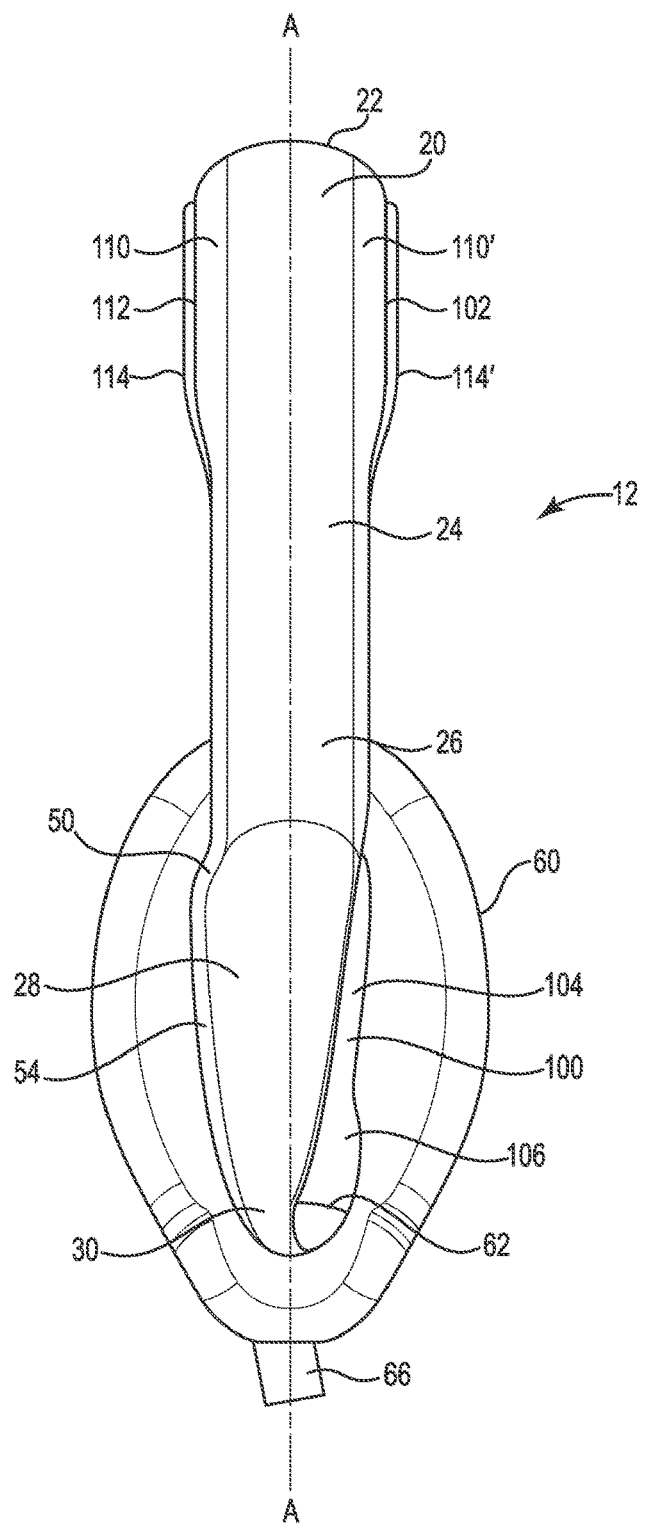
FIG. 4 is a back view of the laryngeal mask of FIGS. 1 and 2 without the gastric tube.
Figure 5:
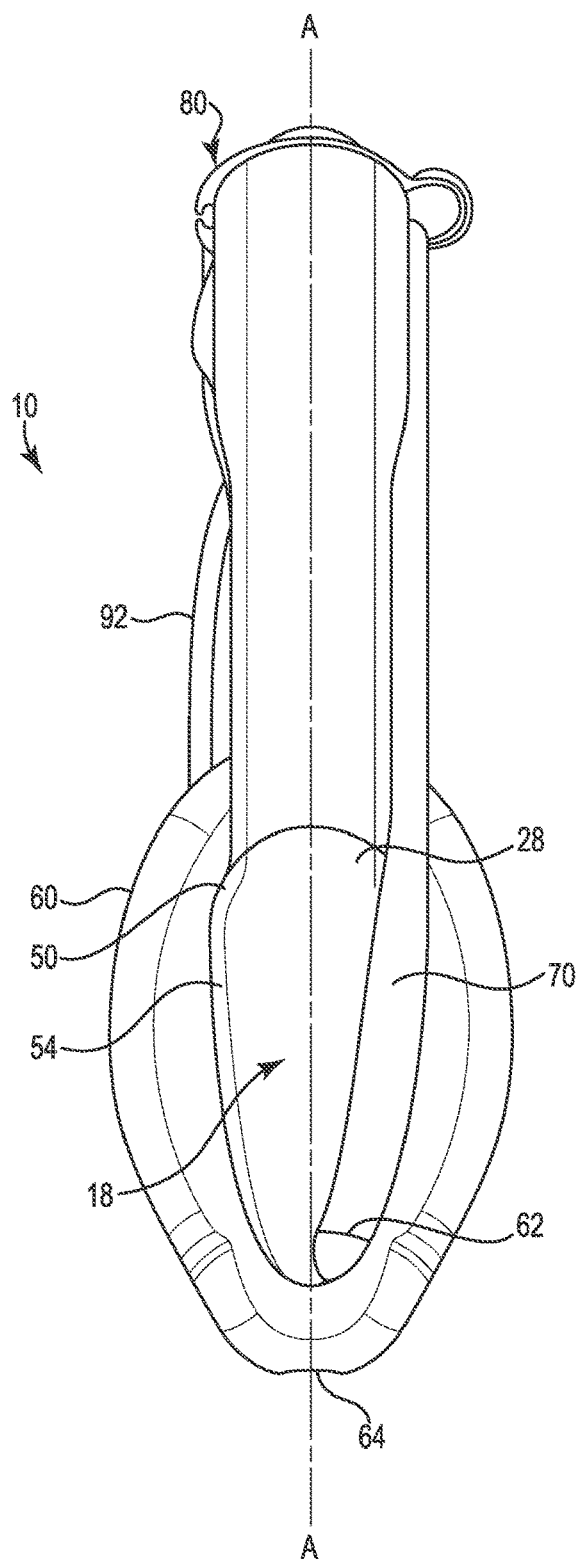
FIG. 5 is a back view of the laryngeal mask of FIGS. 1 and 2 including the gastric tube.

Turning to FIGS. 3-5, FIG. 3 is a right-side perspective view of single piece body 12 of laryngeal mask 10 and FIG. 4 is back view of single piece body 12 of laryngeal mask 10. FIG. 5 is back view of laryngeal mask 10 with gastric tube 70 shown positioned on single piece body 12. Gastric tube 70 is positioned in recess 100. Distal recess portion 104 is wider near proximal aperture 62 to provide more support to the distal end of gastric tube 70 where gastric tube 70 is inserted through proximal aperture 62 into cuff 60. A tubular stub 66 is shown protruding from cuff 60. During manufacture, tubular stub 66 is reversed (turned on itself) and gastric tube 70 is connected and bonded to tubular stub 66.

Gastric tube 70 extends along the outer right-hand side surface of airway tube 14, preferably but not necessarily along the entire length thereof. Gastric tube 70 penetrates a tubular wall 132 of cuff 60, extends through inner volume 134 (shown in FIG. 7), and ends in a connection arrangement at a second location on tubular wall 132 of cuff 60, at the tip of laryngeal mask 10, so as to present distal aperture 64 at the distal end of gastric tube 70. The connection engagement is preferably provided as short stub 66, which in assembly is inverted from the position shown in FIGS. 6 and 7 and glued to the outside of gastric tube 70 at the distal end of gastric tube 70. The tip of laryngeal mask 10 is adapted to engage into the oesophagus of the patient when laryngeal mask 10 is correctly positioned in the patient. Gastric access is possible by inserting a probe, a catheter or other relevant means from the proximal end of gastric tube 70, passing it all the way through gastric tube 70, and out of distal aperture 64.

Gastric tube 70 is accommodated in recess 100 to maintain as much symmetry as possible. Symmetry is to be understood as mirror symmetry with respect to a central plane about which inner lumen 22 is generally mirror symmetric. This central plane corresponds to the longitudinal cross section in FIG. 7 taken along the axis A-A in FIG. 6. As can be seen airway tube 14 has an overall curvature in that central plane so as to preferably fit the anatomy of the patient and allowing correct insertion of laryngeal mask 10 into the patient. The airway tube thus has an inner lumen following a predetermined curve in a central mirror symmetry plane about which the inner lumen is generally mirror symmetrical. The desire for symmetry reflects the fact that the human body generally also exhibits a large degree of mirror symmetry. Though the predetermined curvature is preferably to fit the anatomy, the skilled person will understand that the actual shape of the predetermined curvature is not of importance for the symmetry considerations. The predetermined curvature may therefore include a straight line, e.g. if the airway tube 14 of laryngeal mask 10 is provided with a high degree of flexibility allowing the airway tube 14 to adapt to the anatomy of the patient.

Despite this desire for symmetry it has been found that minor deviations, some of which have already been described above, will provide major advantages for the manufacturing process without compromising the overall function of laryngeal mask 10. Thus, as described above, gastric tube 70 extends along the outer surface of the airway tube 14 in an asymmetrical manner, through said closed tubular wall 132 at a first location arranged asymmetrically with respect to said central plane, through said inner volume 134, and ends in a connection to the closed tubular wall 132 at a second location at the tip part so as to provide a passage through said cuff 60.

However, since for symmetry reasons the off-set of proximal aperture 62 should be kept small, distal recess portion 104 cuts quite deeply into the outer surface of wedge portion 18 close to proximal aperture 62. Accordingly, the wall thickness of wedge portion 18 may be small in the area close to proximal aperture 62, and might not support gastric tube 70 as well as could be desired. It has been found, however, that this can be mitigated by increasing the support of gastric tube 70 along a length of wedge portion 18 away from proximal aperture 62 toward distal end 26 of airway tube 14. Preferably this is done by widening distal recess portion 104 so as to form a protrusion, such as a salient shelf or ledge 106 on the back side of the recess, on which gastric tube 70 may rest and be supported. Gastric tube 70 may be secured to the salient shelf or ledge 106 by gluing. The depth of recess 100 varies along the length of laryngeal mask 10. Ledge 106 preferably only stretches the length of mask portion 16, i.e. until mask portion 16 transitions to airway tube 14. In particular, ledge 106 may be made extra wide for even better support near proximal aperture 62.

FIGS. 6 and 7 are front and sectional views of single piece body 12. Cuff 60 comprises tubular member 132 having a first edge thereof bonded to wedge portion 18 during formation of single piece body 12 and an opposite, second, edge having a bead 140. Cuff 60 also comprises a circumferential groove 136. During assembly bead 140 is mated with groove 136 and bonded thereto to form a seam 142 defining, together with tubular member 132, inner volume 134. Cuff 60 thus comprises inner volume 134 delimited by closed tubular wall 132 so as to define a generally donut or ring shaped or toroidal inner volume, i.e. a closed tubular loop. In the relaxed state, i.e. as molded and glued, but not inflated, cuff 60, and hence inner volume 134, is not toroidal in a strict sense as it is neither circular in cross section of the tubular member nor in the extension along the loop formed by the tubular member. As can be seen in FIG. 7, the cross-section of cuff 60 varies along the length of the closed loop. Moreover, as can be seen in FIG. 6, the closed tubular loop is not circular, but generally elliptical or oval, the oval taken in its literal meaning actually being pointed as an egg towards the distal end of laryngeal mask 10. The pointed distal end of laryngeal mask 10 thus presents a tip. Also shown in FIG. 6 is a longitudinal rib 120 on the surface of breathing tube 14. Inflation tube 92 extends from cuff 60 and is bonded thereto and along rib 120. A wedge base plane 138 is shown on FIG. 7 which is parallel to and traverses seam 142 when cuff 60 is completed. Wedge base Plane 138 is discussed further below with reference to FIG. 11.

With this arrangement it becomes easier to manufacture the laryngeal mask. The airway tube and the mask portion with the cuff may be molded in one single piece. Mounting the gastric tube in this single piece is facilitated by provision of a recess structured to receive the gastric tube. Moreover, the asymmetry provided by inclusion of the gastric tube is advantageous because even though the human body exhibits a great deal of symmetry it is not entirely symmetrical, and the entry to the esophagus is slightly off-set towards the left-hand side of the body. Consequently the asymmetry facilitates the insertion of a catheter or the like via the gastric tube into the esophagus because during insertion, the catheter is guided by the gastric tube and will therefore have a tendency to exit pointing to the left corresponding to the asymmetry of the human body at the entry of the esophagus. This may be further improved if, according to a further preferred embodiment, the depth of the recess varies along the length of the laryngeal mask and widens to provide additional support near the tip of the mask portion.

According to yet a further embodiment, the outer surface of the airway tube presents a protrusion adjacent said recess so as to increase the depth of said recess. This allows the relative deviations from symmetry compared to the dimensions of the laryngeal mask perpendicular to the mirror symmetry plane to be kept small where the dimensions perpendicular to the mirror symmetry plane are small.

The proximal aperture is arranged at the back of the tubular cuff when the laryngeal mask is correctly inserted in the patient. This allows easy insertion of the gastric tube into the cuff before it is joined with the cuff, and provides good access to the proximal and distal apertures when joining the gastric tube to the cuff.

According to another embodiment, the depth variation of the recess comprises a salient shelf provided in an area on the outer surface of the airway tube corresponding to an area where the inner lumen of the airway tube transitions into the mask lumen. Using a salient shelf provides additional support of the gastric tube in selected places. With the additional support for the gastric tube from the salient shelf, the gastric tube itself becomes capable of providing support for other parts of the outer wall of the airway tube. This, in turn, means the outer wall of the airway tube may be made much thinner. When the distal end of the airway tube has a taper towards the mask portion, this means that the gastric tube may be located closer to the mirror image symmetry plane, thus allowing the laryngeal mask to present a higher degree of symmetry even where the airway tube has a taper.

According to another embodiment, the short stub is provided at an angle adapted to point towards the side of the plane in which the distal aperture is off-set, preferably towards the aperture and recess leading to the aperture. This allows easy connection of the short stub to the gastric tube. Furthermore, this configuration ensures a better guiding of the catheter towards the entrance of esophagus.

Figure 8:
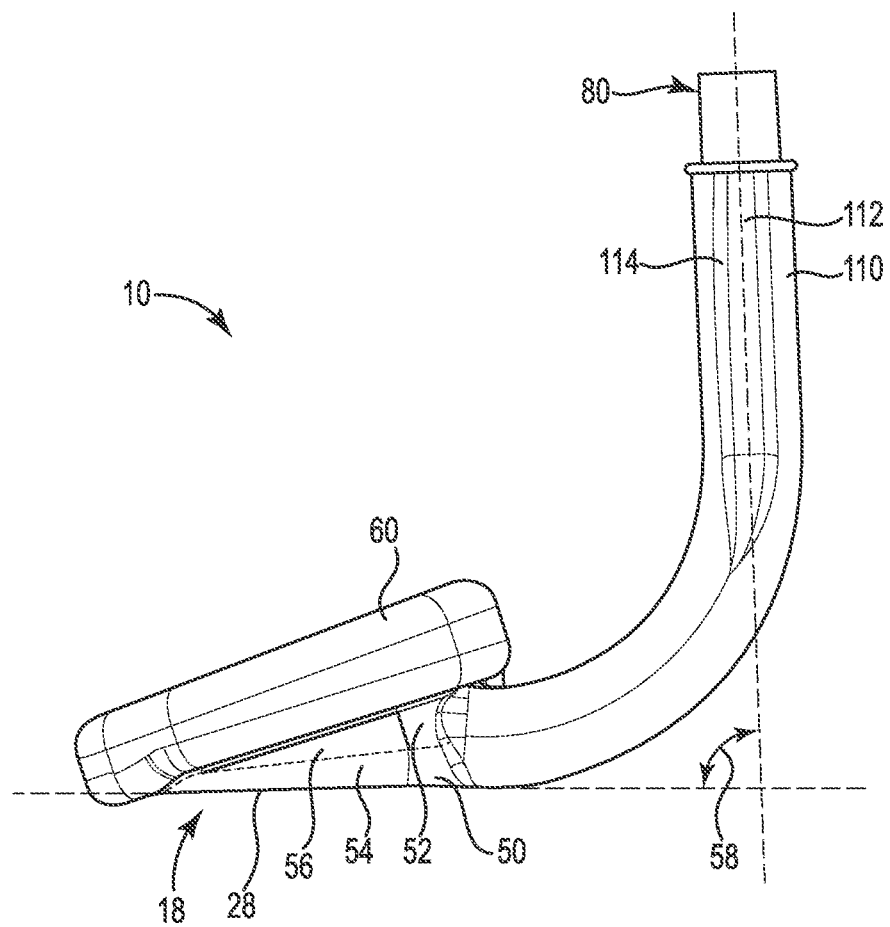
FIG. 8 is a left-side view of the laryngeal mask of FIGS. 1 and 2.
Figure 9:
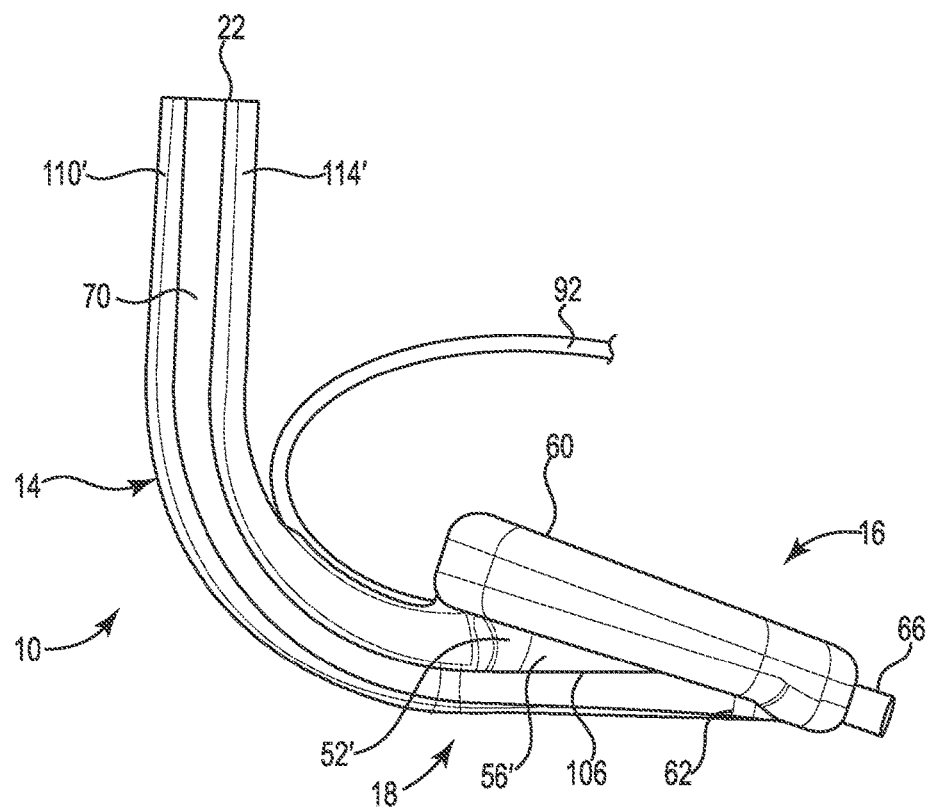
FIG. 9 is a right-side view of the laryngeal mask of FIGS. 1 and 2.

FIGS. 8 and 9 are left-side and right-side views, respectively, of laryngeal mask 10, illustrating the characteristics of the walls of wedge portion 18, FIG. 9 showing the presence of gastric tube 70. FIG. 8 illustrates that airway tube 14 curved, forming an angle 58 between a left-right plane extending longitudinally along stabilization or stabilizing surface 28 and a longitudinal axis at the proximal end of airway tube 14. Preferably, angle 58 is between 80-100 degrees. The combination of the curved section and the wedge portion has shown to make the laryngeal mask stable when placed in a patient, which is very desirable when conducting endoscopic procedures. By contrast with FIG. 9, FIG. 10 is a right-side view of another embodiment of a laryngeal mask, denoted by numeral 200, without said gastric tube.

Figure 10:
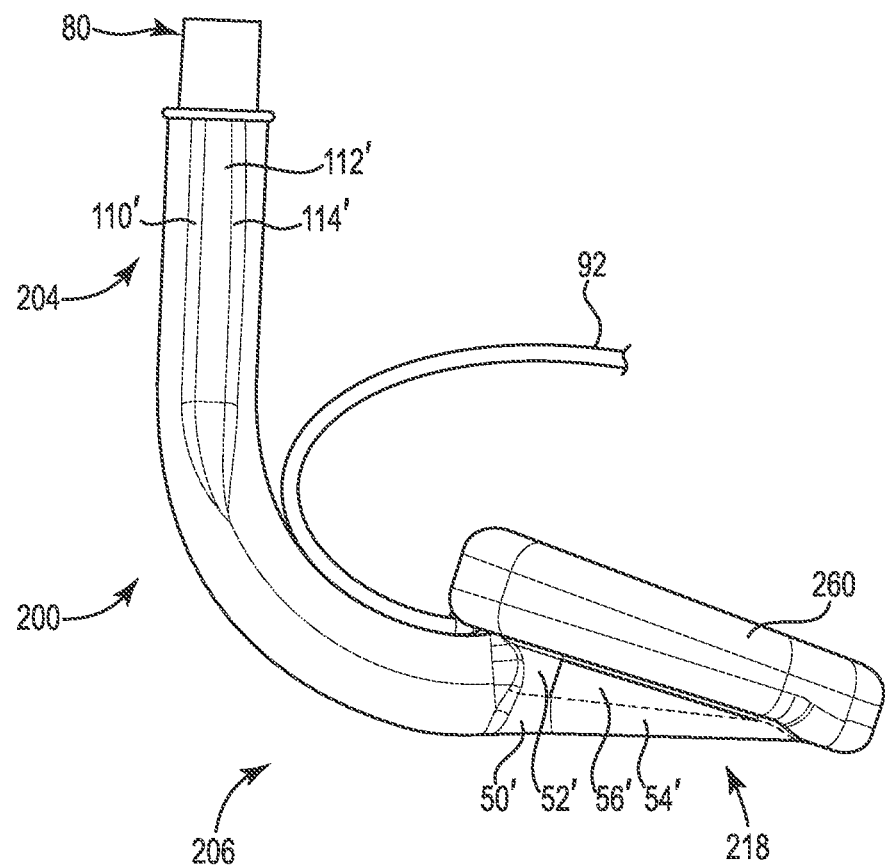
FIG. 10 is a right-side view of another embodiment of a laryngeal mask.
Figure 11:
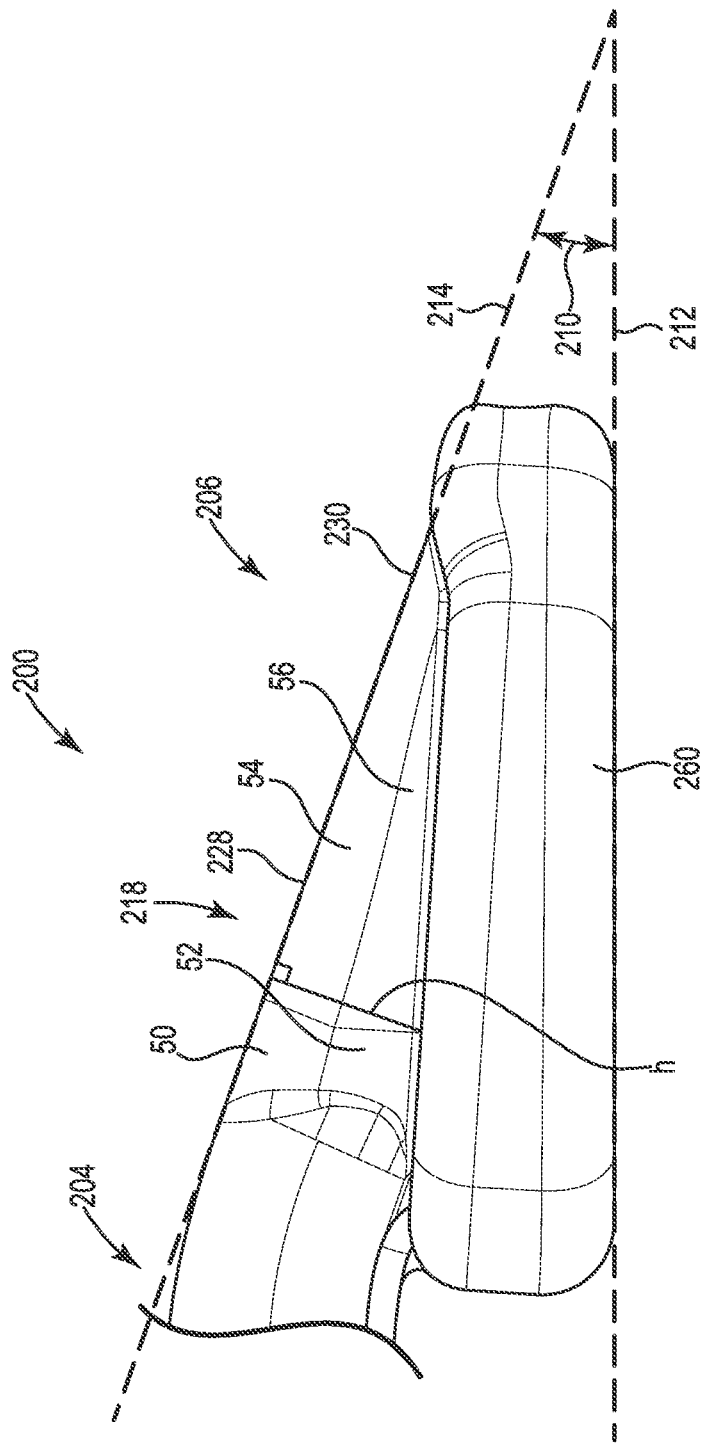
FIG. 11 is a partial right-side view of the laryngeal mask of FIG. 10.
Figure 12:
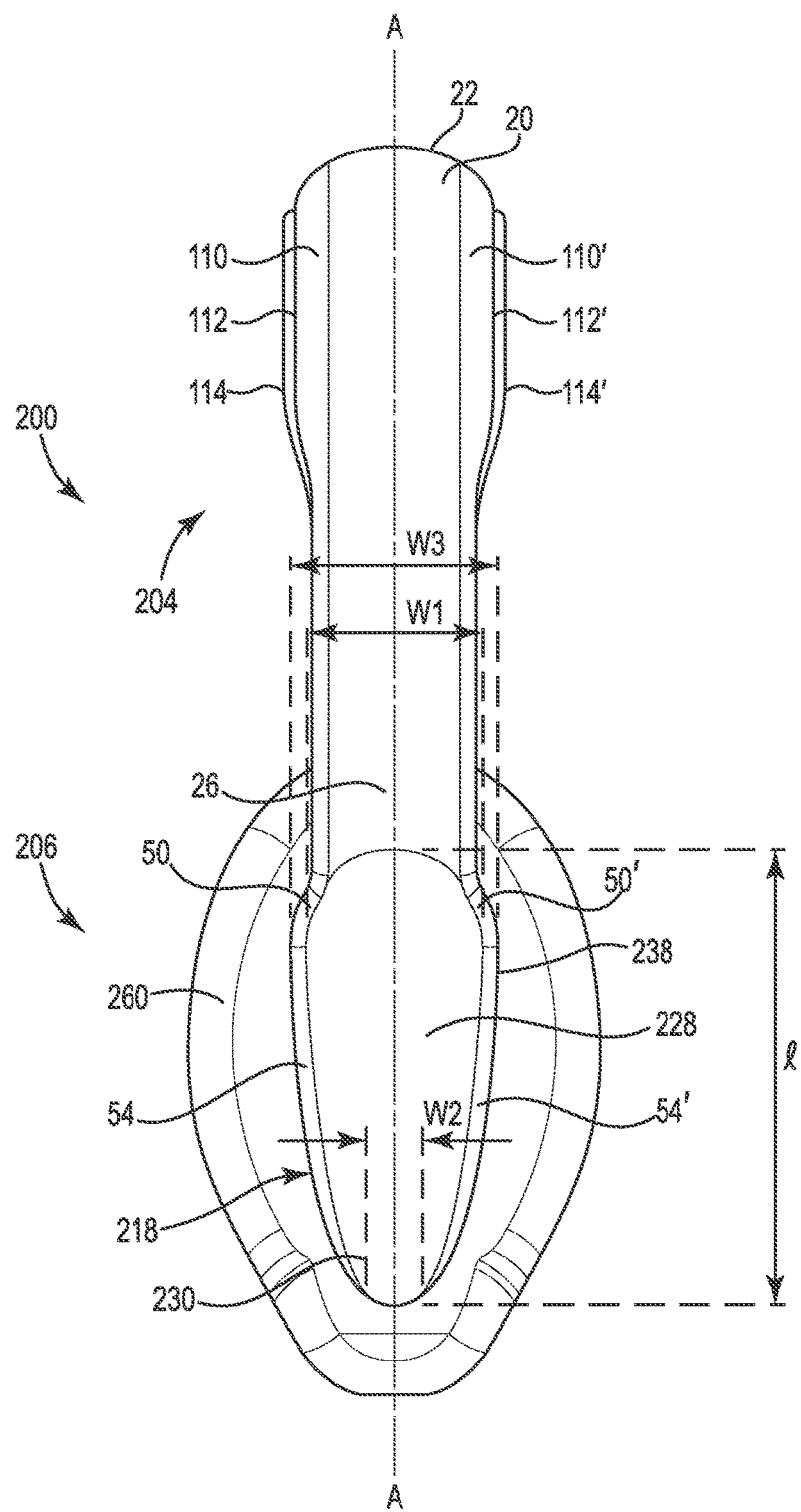
FIG. 12 is a back view of the laryngeal mask of FIG. 10.

FIGS. 10-12, show laryngeal mask 200 comprising a breathing tube 204, and a mask portion 206 having a wedge portion 218, a distal end 230, and an inflatable cuff 260. Breathing tube 204 exhibits protrusions 110', 114' and a recess 112' therebetween. Laryngeal mask 200 is like laryngeal mask 10 except that it does not include a gastric tube and therefore does not require, and does not have, recess portion 104, apertures 62, 64 on inflatable cuff 260, or tubular stub 66.

Turning now to FIGS. 11 and 12, an expanded partial view of laryngeal mask 200 is shown in FIG. 11 to better illustrate wedge portion 218. Stabilizing surface 228 of wedge portion 218, best seen in FIG. 12, is similar to stabilizing surface 28, except that it is longitudinally symmetrical due to the absence of gastric tube 70. Wedge portion 218 comprises stabilizing surface 228, a left shoulder surface formed by left rounded shoulder wall 50 adjacent left shoulder wall 52, and a left edge surface formed by left rounded edge wall 54 adjacent left edge wall 56. On the right side, wedge portion 218 comprises a right shoulder surface formed by right rounded shoulder wall 50' adjacent right shoulder wall 52', and a right edge surface formed by right rounded edge wall 54' adjacent right edge wall 56'. FIG. 11 also illustrates a front plane 212 of inflatable mask 60, 260, which forms an air seal with the anterior (front) side of the patient's laryngopharynx during use, a wedge plane 214 including stabilizing surface 28, 228, which contacts the posterior (back) side of the patient's laryngopharynx, and a wedge angle 210 defined by front plane 212 and wedge plane 214. In some embodiments, wedge angle 210 is between about 10 and 30 degrees. More preferably, wedge angle 210 is between about 15 and 25 degrees. Even more preferably, wedge angle 210 is between about 17.5 and 22.5 degrees. In one embodiment, wedge angle 210 is about 20 degrees. In some embodiments, wedge base plane 138 is parallel to front plane 212, and wedge portion 18, 218 therefore forms an angle between wedge base plane 138 and wedge plane 214 equal to wedge angle 210. However in other embodiments inflatable mask 60, 260 is configured to have a greater cross-sectional area in the front or back, and the wedge walls are correspondingly changed such that wedge base plane 138 is not parallel to front plane 212 (as seen in FIG. 7) yet wedge angle 210 is dimensioned as described above in this paragraph. Wedge portion 18, 218 may have a height h, measured perpendicularly to stabilizing surface 28, 228 from stabilizing surface 28, 228 to point where walls 52 and 56 and wedge base plane 138 intersect. In one embodiment, height h equals 1.0 centimeters.

Turning now to FIG. 12, a back view of laryngeal mask 200 is shown to illustrate stabilizing surface 228 of wedge portion 218. Stabilizing surface 228 is similar to stabilizing surface 28, except that it is longitudinally symmetrical due to the absence of gastric tube 70. Wedge portion 218 comprises stabilizing surface 228, a left shoulder surface formed by left rounded shoulder wall 50 adjacent left shoulder wall 52, and a left edge surface formed by left rounded edge wall 54 adjacent left edge wall 56. On the right side, wedge portion 218 comprises a right shoulder surface formed by right rounded shoulder wall 50' adjacent right shoulder wall 52', and a right edge surface formed by right rounded edge wall 54' adjacent right edge wall 56'. As previously stated, stabilizing surface 228 and wedge portion 218 functions to stabilize mask portion 16 and the dimensions thereof are not arbitrary design choices. One characteristic of the wedge portion is the maximum width aspect ratio. As used herein, the maximum width aspect ratio is the ratio, expressed as a percentage, of the maximum width w1 to the length l of stabilizing surface 28, 228. In the case of the embodiment including a gastric tube, the maximum width is calculated by measuring from a longitudinal centerline passing through stabilizing surface 28, 228 to the maximum width thereof on the side without the gastric tube perpendicularly to the longitudinal centerline to determine the maximum half-width and then multiplying the maximum half-width by 2. In some embodiments, the maximum width aspect ratio is between about 22% to 35%. More preferably, the maximum width aspect ratio is between about 25% to 32%. In one embodiment, the maximum width aspect ratio is about 28.5%.

Another characteristic of the wedge portion is the minimum width aspect ratio. As used herein, the minimum width aspect ratio is the ratio, expressed as a percentage, of the minimum width w2 to the length l of stabilizing surface 28, 228. In the case of the embodiment including a gastric tube, the minimum width is calculated by measuring from a longitudinal centerline passing through stabilizing surface 28, 228 to the minimum width thereof on the side without the gastric tube perpendicularly to the longitudinal centerline to determine the minimum half-width and then multiplying the minimum half-width by 2. In some embodiments, the minimum width aspect ratio is between about 5% and 15%. More preferably, the minimum width aspect ratio is between about 8% to 12%. In one embodiment, the minimum width aspect ratio is between about 10%.

The characteristics of the wedge portion also comprise the width ratio. As used herein, the width ratio is the ratio of the maximum width w1 of stabilizing surface 28, 228 to the corresponding width w3 of wedge portion 18, 218 where it intersects wedge base plane 138 (referred to as the maximum wedge base width), which together with the wedge angle characterize the steepness of the walls of the wedge portion. In some embodiments, the width ratio w1/w3 is between about 0.50 and 0.82. More preferably, the width ratio is between about 0.6 and 0.72. In one embodiment, the width ratio is about 0.67.

The characteristics of the wedge portion with a gastric tube having a larger inner diameter at the proximal end define a unique structure that enhances the use of the laryngeal mask in endoscopic procedures without impairing the benefits to the patient. FIGS. 13 and 14 show an embodiment of a laryngeal mask 300 comprising the single piece body 12 and a gastric tube 302 having a proximal section 302a, an intermediate section 302b and a distal section 302c. The inner diameter of the proximal section 302a is larger than the inner diameter of the distal section 302c. The intermediate section 302b, positioned between the proximal section 302a and the distal section 302c, is conically tapered between. Likewise, the outer diameter of the proximal section 302a is larger than the outer diameter of the distal section 302c. The intermediate section provides a smooth transition between the larger inner diameter of the proximal section 302a and the smaller inner diameter of the distal section 302c. Preferably, the gastric tube 302 is molded or extruded in one piece to ensure a smooth transition between the different inner diameters.

As seen from FIGS. 13 and 14 and described with reference to FIG. 8, the airway tube is curved at angle 58 formed between a left-right plane extending longitudinally along the stabilization surface 28 and a longitudinal axis at the proximal end of the airway tube. Preferably, the angle 58 is between 80-100 degrees. The combination of the curved section and the wedge portion has shown to make the laryngeal mask stable when placed in a patient, which is very desirable when conducting endoscopic procedures via the gastric tube 302 and the airway tube 24. The provision of a gastric tube 302 having a proximal section 302a with a larger inner diameter than the distal section 302c makes it possible to conduct endoscopic procedures with a larger range of endoscopes. Especially endoscopes with a relatively long rigid distal tip is facilitated that would not be able to pass through the curved section of the gastric tube if it had a small diameter.

The proximal section 302a has a curved section 304 and extends along the curve of the airway tube. The distal section 302c extends in parallel with the length of the stabilization surface 28. The intermediate section 302b forms a transition from the curved section 71 of proximal section 302a to the distal section 302c. The proximal part of the intermediate section 302b is slightly curved and the distal part of the intermediate section 302b is substantially straight. The intermediate section 302b is positioned adjacent the proximal end of the posterior cuff surface. The increased inner diameter of the proximal section 302a allows even endoscopes with a relatively long rigid distal tip to be advanced through the curved proximal section 302a. Where the curvature of the proximal tube decrease, the intermediate section 302b forms the transition to the distal section 302c, which has a smaller inner diameter. The smaller inner diameter of the distal section 302c is sufficient to allow endoscopes with a relatively long rigid distal tip to be advanced through the distal section 302c of the gastric tube, because of a much more straight course of the distal section 302c even where it passes through the cuff. In order to maintain the sealing properties of the laryngeal mask 300 in the patient's pharynx it is undesirable to have the same inner diameter for the distal section 302c as is used in the proximal section 302a, because that would affect the function of the wedge portion and the cuff.

FIG. 15 is a side-view of gastric tube 302 showing proximal section 302a, intermediate section 302b and distal section 302c. The gastric tube 302 is shown in a condition before it has been mounted on the single piece body 12 of the laryngeal mask 300. In a preferred embodiment the wall thickness of the gastric tube is 0.7 mm, the inner diameter of the proximal section 302c is 13.0 mm and the inner diameter of the distal section 302c is 9.0 mm. The difference of the inner diameter of the proximal section 302a and the distal section 302c is illustrated by the cross-sectional view of FIGS. 16 and 17.

One example of an endoscope preferred for procedures via the gastric tube 302 comprises a flexible insertion cord with an outer diameter of approximately 8 mm. At the distal end opposing an operating handle, the flexible insertion cord comprises a bending section that may bend in two or more directions. Distal to the bending section is a rigid distal tip with a length of approximately 24 mm. For typical adult sizes of the laryngeal mask 300, the curved proximal section 302a will curve with a radius at approximately 40-60 mm. Therefore, the rigid distal tip of the endoscope would not be able to pass through the curved proximal section 302a if the inner diameter was the same as for the distal section 302c.

The laryngeal mask is preferably used in a method for performing an endoscopic procedure, said method comprising: providing a laryngeal mask having a gastric tube a varying inner tube diameter as described above, inserting the laryngeal mask into a patient, providing a first endoscopic visualization device with an insertion portion and performing an endoscopic procedure via the inner lumen of the laryngeal mask by inserting the insertion portion of the first endoscopic visualization device beyond the vocal cords of the patient, providing a second endoscopic visualization device with an insertion portion and performing an endoscopic procedure via the gastric tube of the laryngeal mask by inserting the insertion portion of the second endoscopic visualization device beyond the esophagus of the patient. It is preferred that the laryngeal mask is inserted to enable ventilation of the patient during a general anesthesia. It is moreover preferred that the general anesthesia is without relaxants. By conducting the procedures during an anesthesia without relaxants the patient's wakeup time is reduced and more procedures can be conducted in less time. Moreover, the costs of the anesthesia is also reduced.

Hence, during one general anesthesia it is possible to perform an Endoscopic Ultrasound-Guided Fine-Needle Aspiration (EUS-FNA) procedure via the gastric tube 302 and an Endobronchial ultrasound transbronchial needle aspiration (EBUS-TBNA) procedure via the airway tube 14. The EUS-FBA procedures is an endoscopic procedure used to obtain detailed images of the digestive tract, including the pancreas and surrounding abdominal organs and tissue samples for analysis. The EBUS-TBNA is an endoscopic procedure that enables visualization and sampling of mediastinal, central or hilar lesions and lymph nodes within the bronchial tree.

The characteristics of the wedge portion define a unique structure that enhances the laryngeal mask by providing useful stabilization properties that benefit the patient. These characteristics, as described above, can be combined in multiple ways, including those described above, as claimed in the claims, and in ways a person having skill in the art will easily determine without undue experimentation based on the foregoing disclosure. The above detailed description and the examples described therein have been presented for the purposes of illustration and description only and not by limitation. It is therefore contemplated that the present disclosure covers any and all modifications, variations or equivalents that fall within the spirit and scope of the basic underlying principles disclosed above and claimed herein.

What is claimed is:

1. A laryngeal mask for use in a patient, the laryngeal mask comprising:
   an airway tube having an inner lumen, an outer surface, a proximal end, a distal end, and a curved section between the proximal end and the distal end;
   a gastric tube which extends along the outer surface of the airway tube, the gastric tube has a first inner diameter along at least a portion of the curved section of the airway tube, which first inner diameter is larger than a second inner diameter of the gastric tube distal to the curved section of the airway tube; and
   a mask portion connected at a proximal end thereof to the distal end of the airway tube and having a distal tip opposite the proximal end, the mask portion comprising:
      an inflatable cuff including an anterior cuff surface configured to contact the patient's tissue when the inflatable cuff is inflated; and
      a wedge portion including a stabilization surface and two walls connected to the inflatable cuff and extending therefrom toward the stabilization surface, the stabilization surface extending from the distal tip of the mask portion toward the distal end of the airway tube at a wedge angle of between about 12 and 30 degrees, the wedge angle formed between the stabilization surface and the anterior cuff surface when the inflatable mask is inflated, wherein the stabilizing surface has a maximum width aspect ratio of between about 22% to 35%, the maximum width aspect ratio being the ratio, expressed as a percentage, of the maximum width w1 to the length l of the stabilizing surface, whereby the stabilization surface is transversely and longitudinally substantially flat to stabilize the laryngeal mask in use.

2. A laryngeal mask as in claim 1, wherein the wedge angle is between about 15 and 25 degrees.

3. A laryngeal mask as in claim 2, wherein the wedge angle is between about 17.5 and 22.5 degrees.

4. A laryngeal mask as in claim 3, wherein the wedge angle is about 20.0 degrees.

5. A laryngeal mask as in claim 1, wherein the maximum width aspect ratio is between about 25% to 32%.

6. A laryngeal mask as in claim 5, wherein the maximum width aspect ratio is between about 25% to 32% and the wedge angle is between about 17.5 and 22.5 degrees.

7. A laryngeal mask as in claim 1, wherein the maximum width aspect ratio is about 28.5%.

8. A laryngeal mask as in claim 1, further comprising a recess on one side of the mask portion, wherein the gastric tube is received in the recess, the inflatable cuff having an inner volume and comprising a proximal aperture, the gastric tube penetrating through the proximal aperture and the inner volume.

9. A laryngeal mask for use in a patient, the laryngeal mask comprising:
   an airway tube having an inner lumen, an outer surface, a proximal end, a distal end, and a curved section between the proximal end and the distal end;
   a gastric tube which extends along the outer surface of the airway tube, the gastric tube has a first inner diameter along at least a portion of the curved section of the airway tube, which first inner diameter is larger than a second inner diameter of the gastric tube distal to the curved section of the airway tube; and
   a mask portion connected at a proximal end thereof to the distal end of the airway tube and having a distal tip opposite the proximal end, the mask portion comprising:
      an inflatable cuff including an anterior cuff surface configured to contact the patient's tissue when the inflatable cuff is inflated; and
      a wedge portion including a stabilization surface and two walls connected to the inflatable cuff and extending therefrom toward the stabilization surface, the stabilization surface extending from the distal tip of the mask portion toward the distal end of the airway tube at a wedge angle of between about 12 and 30 degrees, the wedge angle formed between the stabilization surface and the anterior cuff surface when the inflatable mask is inflated, wherein the stabilizing surface has a minimum width aspect ratio of between about 5% and 15%, the minimum width aspect ratio being the ratio, expressed as a percentage, of the minimum width w2 to the length l of the stabilizing surface, whereby the stabilization surface is transversely and longitudinally substantially flat to stabilize the laryngeal mask in use.

10. A laryngeal mask as in claim 9, wherein the minimum width aspect ratio is between about 8% to 12%.

11. A laryngeal mask as in claim 10, wherein the minimum width aspect ratio is about 10%.

12. A laryngeal mask as in claim 9, wherein the stabilizing surface has a maximum width aspect ratio of between about 22% to 35%, the maximum width aspect ratio being the ratio, expressed as a percentage, of the maximum width w1 to the length l of the stabilizing surface, the minimum width aspect ratio is between about 8% to 12%, and the wedge angle is between about 17.5 and 22.5 degrees.

* * * * *